(12) United States Patent
Shiozawa et al.

(10) Patent No.: US 7,514,211 B2
(45) Date of Patent: Apr. 7, 2009

(54) GENOMIC DNAS PARTICIPATING IN RHEUMATOID ARTHRITIS, METHOD OF DIAGNOSING THE SAME, METHOD OF JUDGING ONSET RISK AND DIAGNOSTIC KIT FOR DETECTING THE SAME

(75) Inventors: Shunichi Shiozawa, 11-6, Takenodai 2-chome, Nishi-ku, Kobe-shi, Hyogo (JP); Koichiro Komai, Hyogo (JP); Hirofumi Yagi, Hyogo (JP); Nao Matsuura, Hyogo (JP)

(73) Assignee: Shunichi Shiozawa, Kobe-Shi (JP)

( * ) Notice: Subject to any disclaimer, the term of this patent is extended or adjusted under 35 U.S.C. 154(b) by 165 days.

(21) Appl. No.: 10/473,368

(22) PCT Filed: Mar. 29, 2002

(86) PCT No.: PCT/JP02/03191

§ 371 (c)(1),
(2), (4) Date: Nov. 18, 2003

(87) PCT Pub. No.: WO02/079466

PCT Pub. Date: Oct. 10, 2002

(65) Prior Publication Data

US 2004/0175706 A1    Sep. 9, 2004

(30) Foreign Application Priority Data

Mar. 30, 2001  (JP) .............................. 2001-102006

(51) Int. Cl.
C12Q 1/68  (2006.01)
C12P 19/34  (2006.01)
C07H 21/02  (2006.01)
C07H 21/04  (2006.01)

(52) U.S. Cl. .................. 435/6; 435/91.1; 435/91.2; 536/23.1; 536/24.3; 536/24.33

(58) Field of Classification Search ........................ None
See application file for complete search history.

(56) References Cited

U.S. PATENT DOCUMENTS

2001/0053519 A1*  12/2001  Fodor et al. .................... 435/6

FOREIGN PATENT DOCUMENTS

WO    00/06769    2/2000
WO    00/17394    3/2000

OTHER PUBLICATIONS

Wacholder et al., "Assessing the Probability That a Positive Report is False: An Approach for Molecular Epidemiology Studies," Journal of the National Cancer Institute," Mar. 17, 2004, vol. 96, No. 6, pp. 434-442.*
Ioannidis et al., "Replication validity of genetic association studies," Nature Genetics, 2001, vol. 29, pp. 306-309.*
Lucentini, J., "Gene Association Studies Typically Wrong," The Scientist, 2004, vol. 18, issue 24, pp. 1-4.*
Venter et al., "The Sequence of the Human Genome," Science, Feb. 2001, vol. 291, pp. 1304-1351.*
Buck et al., "Design Strategies and Performance of Custom DNA Sequencing Primers," Bio Techniques, Sep. 1999, vol. 27, pp. 528-536.*
S. Shiozawa et al., "Genome Kaiseki VIII Mansei Kansetsu Rheumatism to Shikkan Idenshi", Cellular Molecular Medicine, Feb. 2001, vol. 2, No. 2, pp. 181-189.
S. Shiozawa et al., "Kansetsu Rheumatism no Saibogaku Mansei Kansetsu Rheumatism no Shikkan Idenshi", Saibo, 1999, vol. 31, No. 10, pp. 384-389.
S. Shiozawa et al., "An Approach to Identify New Genes in Autoimmune Diseases: Lessions from Rheumatoid Arthiritis", Rev. Immunogenet., 2000, vol. 2, No. 1, pp. 133-139.
C. Bird, Human DNA Sequence from Clone 88D7 on Chromosome Xq25-26.3 Contains F9 (coagulation factor IX (plasma thromboplastic component, Christmas disease, haemophilia B)), dbl oncogene, Nov. 23, 1999, Accession AL033403, Version AL033403.1.

* cited by examiner

Primary Examiner—Young J Kim
(74) Attorney, Agent, or Firm—Wenderoth, Lind & Ponack, L.L.P.

(57) ABSTRACT

A genomic DNA involved in rheumatoid arthritis, a method of diagnosing rheumatoid arthritis or a method of judging onset risk of rheumatoid arthritis, and a diagnostic kit for diagnosing rheumatoid arthritis or judging onset risk of rheumatoid arthritis, which genomic DNA comprises at least one of the following mutations in genomic DNA consisting of the base sequence of SEQ ID NO: 1:

(1) substitution of thymine (t) for cytosine (c) at the position-1987;
(2) substitution of guanine (g) for thymine (t) at the position-3664; and
(3) substitution of cytosine (c) for adenine (a) at the position-3769.

5 Claims, 1 Drawing Sheet

GENOMIC DNAS PARTICIPATING IN RHEUMATOID ARTHRITIS, METHOD OF DIAGNOSING THE SAME, METHOD OF JUDGING ONSET RISK AND DIAGNOSTIC KIT FOR DETECTING THE SAME

This application is a U.S. national stage of International Application No. PCT/JP02/03191 filed Mar. 29, 2002.

TECHNICAL FIELD

The present invention relates to genomic DNAs with mutations, a method of diagnosing human rheumatoid arthritis by using the mutations, a method of judging onset risk thereof, and a diagnostic kit for detecting the same.

BACKGROUND ART

Rheumatoid arthritis (RA) has a cardinal symptom of multiple erosive osteoarthritis, and is also a systemic inflammatory disease with an unknown etiology, simultaneously disturbing multiple organs. RA progresses chronically with periods of repeated remission and exacerbation. Untreated RA causes a destruction and a deformation of joint, later presenting functional disorders of motor apparatus. Sometimes it threatens lives of patients. Consequently, patients with RA have to bear large, lifelong physical and mental burdens.

RA results in a large variety of symptoms, and the diagnostic criteria of the American College of Rheumatology are widely used for its diagnosis. However, development of an onset state of RA is generally very slow, requiring a period from several weeks to several months. According to a judgment by means of an existence of rheumatoid factor, which is an objective index in the diagnostic criteria of American College of Rheumatology, a positive rate is 33% within 3 months and around 88% even after 12 months or more [Chiryo, 73(3): 23-27, 1991]. This indicates that RA cannot be diagnosed definitively at present. An attempt to diagnose rheumatoid arthritis by detecting a serum rheumatoid arthritis associated antigen IgM in a patient through a reaction with recombinant antigen has been performed (JP-A-10-513257).

In a treatment of RA, a therapeutic procedure to be selected is generally varied depending on a progression stage of symptoms in the disease state. Generally, in an early stage during which a definite diagnosis cannot be made, a nonsteroidal antiinflammatory drug (NSAID) is administered; and in a case in which a definite diagnosis can be made, a disease-modifying antirheumatic drug (DMARD) is administered in addition to the NSAID. In particular in an early stage of RA onset, since it is difficult to make a definite diagnosis at present, the NSAID is administered, and at the same time, an effort is made to identify this disease from other rheumatic diseases including collagen disease, by carefully observing the symptom and procession. In a case in which the symptoms continue to progress, steroids may be administered, and a pharmacotherapy for pain together with a physiotherapy and an orthotic therapy are performed in order to maintain and ameliorate joint functions. In addition, in a case in which daily life is inconvenienced by a joint disruption, a surgical therapy may be performed.

Though aspects of arthritis and joint disruption, which are the causes of RA, in particular their pathological processes, are gradually being elucidated through a variety of studies, RA is still thought to be a disease which develops and progresses after an onset caused by cooperation with large number of causative factors including a living environment. For that reason, in order to perform a more exact elucidation of the disease and a proper therapy thereof, an essential part of interactions of the multiple factors involved has to be established. Since RA is a disease with an incident rate of 1% or less in the world (N. Engl. J. Med., 322: 1277-1289, 1990), but siblings of the patient develop the disease at a frequency of 8% or more (Cell, 85: 311-318, 1996), one of the causative factor is suspected to be some genetic factor. Further, since an environment is thought to be one of the causative factors, the onset may be delayed or prevented by paying attention to the daily life style such as diet, viral infections and stress, if the onset risk can be known in advance. Further, by making an earlier diagnosis and providing an appropriate treatment in an earlier stage, progression of RA can be delayed and prognosis can be expected to be improved.

In the international publication, WO98/51794, the inventors of the present invention performed linkage analyses of patients with RA and their sibs using a microsatellite marker, and identified three gene loci involved where genes causative of rheumatoid arthritis are positioned. The following causative genes have been identified:

(1) A gene causative of rheumatoid arthritis located no more than ±1 centimorgan apart from a DNA sequence hybridizable with microsatellite markers D1S214 and/or D1S253 in human chromosome 1.

(2) A gene causative of rheumatoid arthritis located no more than ±1 centimorgan apart from a DNA sequence hybridizable with microsatellite marker D8S556 in human chromosome 8.

(3) A gene causative of rheumatoid arthritis located no more than ±1 centimorgan apart from a DNA sequence hybridizable with microsatellite markers DXS1001, DXS1047, DXS1205, DXS1227 and/or DXS1232 in human chromosome X.

The present inventors further extended the study on the causative gene (3) described above, and found that a specific mutation (2 Exon deleted mutation) of the Db1 proto-oncogene of chromosome X [EMBO J. 7(8): 2465-2473, 1988] was related to the onset state of RA. They then filed the patent application (PCT/JP00/01697).

An object of the present invention is to elucidate further mutations in human Db1 gene and their relations to an onset or an onset risk of RA; and provides a method for precisely diagnosing the onset or the onset risk of RA by utilizing such mutations. Another object of the present invention is to provide a diagnostic kit useful for detecting a genomic DNA which is a mutated Db1 gene associating with RA.

DISCLOSURE OF INVENTION

Under these circumstances, the present inventors have continued extensive studies and found the following mutations in the genomic DNA represented by SEQ ID NO: 1, which showed a base sequence of intron 24-exon 24-intron 23 of the Db1 gene in cells obtained from examinees: (1) Substitution of thymine (t) for cytosine (c) at the position-1987; (2) Substitution of guanine (g) for thymine (t) at the position-3664, and (3) Substitution of cytosine (c) for adenine (a) at the position-3769.

More specifically, the base (c) at the position-1987 is located in the intron 24, and the bases (t) and (a) at the position-3664 and the position-3769 are located in the intron 23. Previously, it has been known that there are several genomic genes involved in the onset of RA, and the mutated genomic DNA of the present invention is now known to be partially the cause of the RA onset. Such a relationship between single base substitution mutation and diseases is known in other cases such as the gene causative of type II diabetes mellitus (Nature Genetics, 26: 163-175, 2000).

The present inventors have found from these studies that a method of diagnosing RA, a method of judging the onset risk of RA, and a diagnostic kit for detecting these mutations, by using the mutations of the Db1 gene in cells obtained from examinees as a index, are useful, and accomplished the present invention. Further, the present invention is useful for developments of novel preventive or therapeutic methods and drugs for the treatment of rheumatoid arthritis.

In the present specification, unless otherwise specifially noted, a, c, g and t mean the bases adenine, cytosine, guanine and thymine, respectively.

Further, SEQ ID NO: 1 corresponds to the sequence from the position-55,823 to the position-59,696 of the sequence registered in GenBank as the human genome of the X chromosome, q25-26.3 region containing the genomic DNA of the Db1 gene (GenBank accession No. AL033403). In this connection, the sequence registered in GenBank has the following properties: The complementary strand thereof is a +strand; it is translated from the position-115,837 to 5' direction; and it transcribes mRNA of the GenBank accession No. X12556.

The method of diagnosing RA, the method of judging onset risk thereof, and the diagnostic kit for detecting the same in the present invention, detects at least one of the mutations in the genomic DNA previously described.

BRIEF DESERIPTION OF DRAWINGS

BEST MODE FOR CARRYING OUT THE INVENTION

Figure 1:
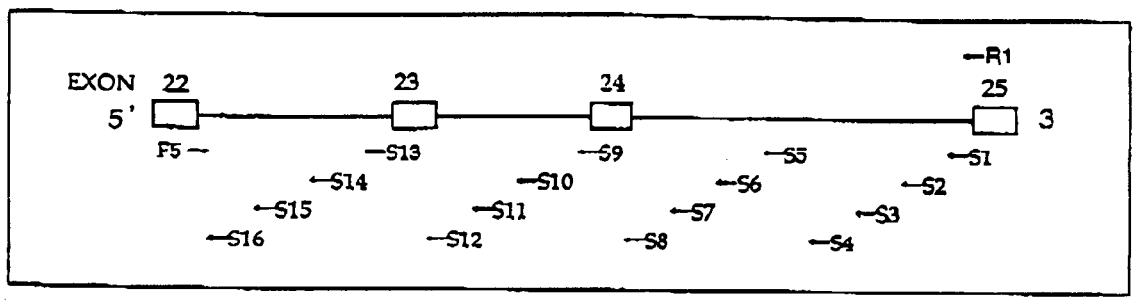
FIG. 1 is a schematic drawing showing a relationship between the primers used for sequence determination of the causative gene of RA and the genomic DNA.

Identification of a mutant genomic DNA and diagnosis of RA or judgment of onset risk of RA can be made, for example, as described below.

A genomic DNA of an examinee can be obtained by the conventional method from any human cells, for example, hair, various organs, peripheral lymphocytes and synovial cells. It can also be obtained from cultured and proliferated cells. In addition, the thus obtained genomic DNA can be used after being amplified by using the conventional gene amplification methods such as PCR (Polymerase chain reaction), NASBA (Nucleic acid sequence based amplification), TMA (Transcription-mediated amplification) and SDA (Strand displacement amplification).

Detection method for genomic variants is not particularly limited. It includes, for example, allele specific oligonucleotide probe method, oligonucleotide ligation assay method, PCR-SSCP method, PCR-CFLP method, PCR-PHFA method, invader method, RCA (Rolling circle amplification) method and primer oligo base extension method.

In the case of detecting mutations by using the PCR method, a PCR primer, which can amplify the region containing the mutated positions in SEQ ID NO: 1, is synthesized; and then direct sequencing of the PCR product amplified from a genomic DNA of the examinee is carried out to determine the mutation. By detecting at least one mutation described above in the genomic DNA of SEQ ID NO: 1, diagnosis of RA of the examinee or onset risk thereof can then be judged precisely.

The primer used in the present invention can be prepared conventionally by using a DNA synthesizer or the like.

Further, the mutations described above can also be detected by using a microarray equipped with oligonucleotides consisting of a normal sequence and a mutated sequence in the mutation site penumbra.

Moreover, the mutation (t→g) at the position-3664 can also be detected, as shown in the Examples, by amplifying a +strand of the genomic DNK using a synthetic oligonucleotide containing the mutation site thereof (SEQ ID NO: 2 and SEQ ID NO: 3) as a primer in PCR, cleaving the PCR product with the restriction enzyme Hinf-I, and examining whether the PCR product is fragmented into two fragments or not (RFLP analysis). Namely, the normal sequence penumbral to the position-3664 in the complementary strand of SEQ ID NO: 1 is 5'-gaatc-3', and is cleaved by Hinf-I (recognition sequence 5'-g↓antc-3'). On the other hand, the mutated sequence penumbral to the position-3664 in the complementary strand of SE ID NO: 1 is 5'-gcatc-3', and is not cleaved by Hinf-I.

A diagnostic kit of the present invention is not particularly limited as long as it contains a reagent such as primer and probe, which can detect at least one mutation of the genomic DNA described above, and can be obtained by further combining other additional reagents.

Examples of the kit include a combination of a primer which is designed to amplify the genomic region containing at least one mutation described above, and further at least one reagent necessary for detecting the mutation including a prove which is designed to detect the genomic region containing at least one mutation described above, a restriction enzyme and a reagent used for base sequence determination methods such as Maxam-Gilbert method and chain termination method. Preferably, a kit comprising a fluorescence labeled dideoxynucleotide is further included.

Diagnosis of RA or onset risk thereof can be performed precisely by using the diagnostic kit.

The diagnostic kit of the present invention can be constructed, for example, in the case of a kit for RFLP analysis of the mutation at the position-3664, by a primer set consisting of base sequences of SEQ ID NO: 2 and SEQ ID NO: 3, restriction enzyme Hinf-I, DNA synthase, and the like. Further, proper buffer, washing solution and the like, which do not disturb the detection of mutation, may be added.

EXAMPLES

The present invention will be further explained in detail and specifically with illustrating Examples, but is not construed to be limited to the following Examples.

Example 1

Specifying Gene Mutation

Ninety subjects from 30 genealogies, each genealogy consisting of 2 patients with RA and one healthy subject, were selected for analysis. Genomic DNA was extracted from the peripheral blood. After amplifying the region with about 5.3 kbp penumbral to the exon 23 and 24 which correspond to 223 bp deficient region of Db1 gene cDNA by PCR, the base sequence was determined by Dye Terminator method using a sequence primer (FIG. 1) which was designed based on the previously known genomic sequence (Acc. No. AL033403.1). In the statistical analysis, chi-square test ($\chi^2$-test) by the percentage method was used for the test of significance. Base sequence of each primer set used for the PCR is shown as follows:

F5/RE1: 5'-taacagaacgggataagt-3' (SEQ ID NO: 4)

5'-ccaagtgggtagatttccaa-3' (SEQ ID NO: 5)

FE1/RE2: 5'-caaaagctcacttagtt-3' (SEQ ID NO: 6)

5'-ggcttactcctaatggc-3' (SEQ ID NO: 7)

FE2/S5: 5'-cttctcaccttgtggtaaat-3' (SEQ ID NO: 8)

5'-catttgggaaacggtaaagt-3' (SEQ ID NO: 9)

S6AS/S2: 5'-gtggcgcatgcctgtaat-3' (SEQ ID NO: 10)

5'-gcaaggtcaacctacatt-3' (SEQ ID NO: 11)

S3AS/R1: 5'-tggtatataggttacatctattgata-3' (SEQ ID NO: 12)

5'-gctacttgccatttgac-3' (SEQ ID NO: 13)

As the results, 15 positions of SNPs in the intron region were confirmed. Each frequency is shown in Table 1. According to the results of chi-square test, a significant difference in the frequency between the patient with RA and the healthy subject was recognized (p<0.05) in three positions, i.e. nt2632+106 (t→g), nt2632+211 (a→c) and nt2745+576 (g→a). A nomination, e.g. nt2632+106 (t→g), indicates that the intron base t at the 106-position from the genomic base (terminal base in the exon) corresponding to the base at the 2632-position in cDNA sense strand is mutated to g. This corresponds to a→c mutation at the position-3769 in SEQ ID NO: 1. Similarly, nt2632+211 (a→c) corresponds to t→g mutation at the position-3664 in SEQ ID NO: 1, and nt2745+576 (g→a) corresponds to at mutation at the position-1987 in SEQ ID NO: 1.

TABLE 1

| | | nt2522 + 136 (A→G) | nt2522 + 235 (A→G) | nt2522 + 394 (C→T) | nt2522 + 556 (A→G) | nt2522 + 764 (G→A) |
|---|---|---|---|---|---|---|
| Patients with RA | Patients with mutation | 14 | 15 | 1 | 15 | 15 |
| | n | 33 | 43 | 42 | 46 | 45 |
| | Frequency (%) | 42.42 | 34.88 | 2.38 | 32.61 | 33.33 |
| Healthy subjects | Subjects with mutation | 5 | 5 | 0 | 4 | 4 |
| | n | 15 | 18 | 19 | 18 | 18 |
| | Frequency (%) | 33.33 | 27.78 | 0 | 22.22 | 22.22 |

| | | nt2632 + 106 (T→G) | nt2632 + 191 (T→A) | nt2632 + 211 (A→C) | nt2745 + 375 (A→G) | nt2745 + 576 (G→A) |
|---|---|---|---|---|---|---|
| Patients with RA | Patients with mutation | 19 | 0 | 19 | 0 | 20 |
| | n | 45 | 32 | 39 | 54 | 54 |
| | Frequency (%) | 42.22 | 0 | 48.72 | 0 | 37.04 |
| Healthy subjects | Subjects with mutation | 4 | 1 | 2 | 0 | 6 |
| | n | 17 | 12 | 14 | 24 | 24 |
| | Frequency (%) | 23.53 | 8.33 | 14.29 | 0 | 25 |

| | | nt2745 + 655 (A→G) | nt2745 + 1368 (T→C) | nt2745 + 1485 (T→C) | nt2745 + 1527 (C→T) | nt2745 + 1921 (A→G) |
|---|---|---|---|---|---|---|
| Patients with RA | Patients with mutation | 2 | 14 | 10 | 14 | 13 |
| | n | 54 | 31 | 28 | 32 | 46 |
| | Frequency (%) | 3.7 | 45.16 | 35.71 | 43.75 | 28.26 |
| Healthy subjects | Subjects with mutation | 1 | 4 | 2 | 4 | 4 |
| | n | 26 | 10 | 8 | 11 | 23 |
| | Frequency (%) | 3.85 | 40 | 25 | 36.36 | 17.39 |

Example 2

RFLP Analysis of t→g Mutation at the Position-3664 in SEQ ID NO: 1

A genomic DNA consisting of 371 bp was isolated by PCR using DNA primers represented by the following sequences:

```
Db1F15:  5'-ttggaaatctacccacttgg-3'    (SEQ ID NO: 2)

Db1R11:  5'-aaaccaacggtaagtgaaatg-3'   (SEQ ID NO: 3)
``` which were synthesized according to the known sequences, as well as using the reaction composition and conditions as follows.

| Genomic DNA | 1 | µl |
|---|---|---|
| PCR buffer II (Applied Biosystems Inc.) | 2.5 | |
| 25 mM MgCl$_2$ | 1.5 | |
| 2 mM dNTP | 2.5 | |
| 10 pmol/µl sense primer | 0.5 | |
| 10 pmol/µl antisense primer | 0.5 | |
| Gold Taq polymerase | 0.25 | |
| Sterilized water | 16.25 | |
| Reaction conditions: | | |

(95° C./12 min.) × 1
(94° C./30 sec., 50° C./30 sec., 72° C./1 min.) × 30

The thus obtained DNA-amplified reaction mixture was reacted at 37° C. for 1 hour with a restriction enzyme Hinf-I (New England Biolabs Inc., recognition sequence: 5'-G ↓ ANTC-3') using the reaction composition described below to digest completely, and analyzed by the conventional manner using 2.0% agarose gel electrophoresis and ethidium bromide staining.

| PCR reaction mixture | 10 | µl |
|---|---|---|
| Hinf-I | 2 | µl |
| Reaction buffer (NE Buffer II) | 1.5 | µl |
| Sterilized water | 1.5 | µl |

Figure 2:
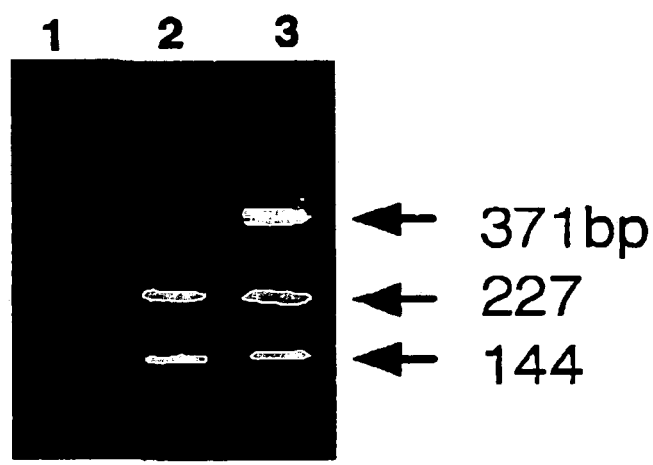
FIG. 2 is electrophoretic patterns after Hinf-I treatment of PCR products amplified by using the primers consisting of base sequences of SEQ ID NO: 2 and SEQ ID NO: 3. Lane 1 indicates a PCR product derived from a homologous variant Db1 gene, lane 2 indicates PCR products derived from a normal (wild type) Db1 gene, and lane 3 indicates PCR products derived from a heterologous variant Db1 gene.

Results are shown in FIG. 2. Lane 2 is an electrophoretic pattern of the PCR product after the Hinf-I treatment obtained by using the normal Db1 gene as a template wherein the sequence is cleaved to 227 bp and 144 bp by the Hinf-I recognition sequence (5'-gaatc-3') at the position-3664 (nt2632+211) penumbra. Lane 1 is an electrophoretic pattern of the PCR product derived from the homologous variant Db1 gene wherein no cleavage occurs due to disappearance of the Hinf-I recognition sequence by t→g mutation at the position-3664 (a→c mutation of nt2632+211). Lane 3 is an electrophoretic pattern of the PCR product derived from the heterologous variant Db1 gene. Since a fragment having the Hinf-I recognition sequence and a fragment without having the Hinf-I recognition sequence were amplified, 3 fragments consisting of a non-cleaved fragment of 377 bp and further cleaved 2 fragments of 227 bp and 144 bp were simultaneously detected.

INDUSTRIAL APPLICABILITY

The present invention relates to genomic DNAs with mutations associated with human rheumatoid arthritis, a method of diagnosing human rheumatoid arthritis by using these mutations, a method of judging onset risk thereof, and a diagnostic kit for detecting the same. The present invention is useful for detecting onset of rheumatoid arthritis or onset risk thereof precisely, simply and exactly. Further, the present invention is useful for, developing novel preventive and therapeutic methods and therapeutic drugs for rheumatoid arthritis.

---

The invention claimed is:

1. An isolated DNA sequence involved in rheumatoid arthritis, which consists of the nucleic acid sequence of SEQ ID NO: 1, and said isolated DNA sequence comprises at least one of the following mutations (1), (2) and (3):
   (1) substitution of thymine (t) for cytosine (c) at position-1987;
   (2) substitution of guanine (g) for thymine (t) at position-3664; and
   (3) substitution of cytosine (c) for adenine (a) at position-3769.

2. The isolated DNA sequence of claim 1, which comprises any two of the mutations (1), (2) and (3).

3. The isolated DNA sequence of claim 1, which comprises the mutations (1), (2) and (3).

4. A diagnostic kit for diagnosing rheumatoid arthritis, which comprises a PCR reagent comprising a primer set consisting of the nucleic acid sequence of SEQ ID NOS: 2 and 3 and restriction enzyme Hinf-I.

5. A method of diagnosing rheumatoid arthritis, which comprises detecting the isolated DNA sequence of claim 1, 2 or 3 in a sample from a subject, and concluding that the subject has an increased likelihood of having a diagnosis of rheumatoid arthritis when the isolated DNA is detected.

* * * * *

SEQUENCE LISTING

```
<160> NUMBER OF SEQ ID NOS: 13

<210> SEQ ID NO 1
<211> LENGTH: 3874
<212> TYPE: DNA
<213> ORGANISM: Homo sapiens
<300> PUBLICATION INFORMATION:
<308> DATABASE ACCESSION NUMBER: GenBank/AL033403.1
<309> DATABASE ENTRY DATE: 1999-11-23

<400> SEQUENCE: 1
ctacaaggga agcagcaccc attattgctc agtttacaac ttgaccaagt gaagccaaaa        60
gagcaggtca ttccagcttc ttgttttggc agggaagaag ggtgtatgga atacattgtg       120
ttgctctttt atatgttttc cttagtagca catctcagag aattattgga caaagagaga       180
gaaactaata ggttttttcta tattcccatc ctctgtgatt aaagcattct tcaatttgc       240 atatttactt tatcttctga taccatagct agaaaaaaaa atgcctactt aaaactgagt       300
tctttacaat gccttcatag atcatctaca gcaaacggtt aaacacaaac tggcttcctc       360
tgactttttg ctcgcattta acaactacta ctatccattc catccccagc taacattaat       420
taaagaaatt aaacttcttt ttattattag tctaagcctg agattcccaa agtgtgggag       480
acagactgtt gtgggttcct gagacccttt caaggggtct gcaaggtcaa cctacattaa       540
```

```
gacactatttt gccttttttca ctctcatcct ctcacaagta cacagtggag ttttctagag      600
gatactaggt gtatggtagc acaacaaatt gaatgcaaaa gtggatatga gaattcacct        660
tttactgagc cagaagttaa agtgatttac aaaagtattt cttttgtaag tatttaagta        720
tttaaatcag tcttctcact gattttttatt ttgaaaaatg taacttttta aacaaaaatc      780
ttattgatat aaacttacaa tgggtttatt aatattttta aacaattatt acattcaaaa        840
ttttgtattt cttagtttta tcacatggta aatatcaata gatgtaacct atataccatg        900
gaatactctg cagccataaa aagaaatgca atcatgtcct ttgcagcaag gtggatgcag        960
ctggaaaccg ttatcctaag caaattaacg caggaacaga aaaccaaata ccacgtgttc       1020
tcacttataa gtggggcta agcattgggt acacgtggac acaaagatgg gcacaatgaa        1080
cactggggac tactagaggg aggaaagagg gttggcagaa gggctgaaaa actacatgtt       1140
gggtactatg ctcactacct gggtgacagg accattcata ctccaaatct cagcatcacg       1200
cagtattccc atgtaacaaa accttacaca tgtacctcct gaatctaaaa taaaagttga       1260
aagtattttt taaaagatat aacctacata acaagagtt ctttgggggtt ttcaattttc       1320
aaggatgtaa aggcttcttt cattaaaaag tttgggaact gcaggtatag acaattaact       1380
ctggacaaat atcttaccag atctaagtct cagtttcctc ctctgtaaat tgaaggtaat       1440
aaagcccgct cttttttcata ctaatactgt gaatattaat tgagaaatca tttgggaaac     1500
ggtaaactat cacacaaata tgtattatgg tcatcatagt attaggagaa acaatatcta       1560
ctttttttaaa gactgcattt cagagtcaat gctgtacagc tttgtgatta tccatgccat     1620
tatccttttt tttttttttt ttttttttg agacagagtt tcgctcttgt tgcccaggct        1680
ggagtgcaag ggactatct cagctcactg caacctgcac ctcctgggtt caagcgattc        1740
tcctgcctca gcctcctgaa tagctgggat tacaggcatg cgccaccaca accgcctaat       1800
tttgtatttt tagtagagac gaggtttacc ctcttatact aacagtagaa ctgccaaatg       1860
taattgattc ctctgaaggg caccaaggag cactctacct ccaagcatca ctcctaccctt     1920
ccaagctggt gactttagaa aagtagggat ttactcccaa acagtcctac ctcctcttta       1980
atagcccact ggtatcctac caacttgcaa actattcctt ctataaacac tttaacctta       2040
aagcaacctc ctttaattt acagggtgct cccttgctct aatatgctga gattttatat        2100
cattagtgta tttttgagaa cacactaaaa tatatccccc agatgttatt aaatcgtttt       2160
taatgtataa tgcttatttc ctttattttc taatctggaa tccaaactgg ttttttaaagt     2220
gtatttgaag cccctttgtt ctctgatttt atttcacatg cctggatgga aaacacagtg      2280
gtgaagctct actaaagata aaactgggat tttagagatt tggaaagatt gactatctat      2340
ttcatcaaca tcagcagaag ctctatgtat aggtcaaaca ggttctactt aaagacagaa      2400
gtgcttcctg atgttcataa taagatttat ttcaactatt ttagcaatgg cttactccta      2460
atggcctcaa ggatgctgac aaaagattgc ccctatgtgc tccacctata tttcatcagt     2520
aaaactgcct caataatttt aatttactat attattacta accatgaggg gcctatttttc    2580
ttcttcattt tcatcataag tagggtagaa atagttgctt gaccattccg caggttcttc     2640
agagatttct gcagattgtg atgcctcagt ccaaactata agaaaagtgt ggaatgtggc      2700
agttacttca tggtgctaat ttaccacaag gtgagaagta aaactagctg taatccttta      2760
aaaagttgaa tttaaaaaaa tggattaacc aatctaatgt aagcagcaaa ttaacagatc      2820
tcatcctggc cacattaaac tattcatgca acctgggaaa agtcattgtc atctttttct      2880
aacttggttt cctcacctgt caaatgaagg cattagtact atgctctctc cttacttctt      2940
```

```
tgggggccac agcatagatg acctgaggga agtgacctt  aattggataa atggaaactc    3000
tacaaggcta tcattacctt tttctcctca accagtagag aactcttcca tattaaggat    3060
catcatatta aagtgttgag tatcaggcac tctgttaggc atttctccaa agaagtctat    3120
gctgttgatc ctagagttgt ttaggtgatc ctcatgtatg cttctacagc acttcgtact    3180
tccctgctgt aacactcgcc aaatttactt ttaattgctt gtttaactat ctttctattc    3240
tcctagcttc atgaggatgg cagctgagtg tatcctagtt agactatatg cctagcactt    3300
tgcataactc ctggaatgca gatcatgcta tgtcaatatt tgttgaatta aataaagtat    3360
ttaaaatcac ttcaaataaa accattcaca gaggaagaat aaatatttcg gctgttaatg    3420
actcttctct attcattaaa ccaacggtaa gtgaaatgcg cattccttga agccagtata    3480
tatgttttat tcatcactat atcctttata gcaggggttc ccaaacttga ccatgcatca    3540
aaatcacaga gagagcctgt taaaactcaa gtggctgggc cttgttccca gagtttctga    3600
tccagaaggt ctgaatagag caagagaatt tgtcttctgt aaaagtttcc aggtgatgtt    3660
gattctagtg gtccagggac cacactttga caaccaatac tctctagtgc ccatcagagt    3720
gtcctgcata tgcaagacat gagagcctta taaaaatggg ttaactgtat tttgtttata    3780
caaaaatacc aagtgggtag atttccaaat taataatacg aggtaaaaat ttgcacaccc    3840
atgagtctcg tcttaagatg accatgacac atac                                3874

<210> SEQ ID NO 2
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 2
ttggaaatct acccacttgg                                                  20

<210> SEQ ID NO 3
<211> LENGTH: 21
<212> TYPE: DNA
<213> ORGANISM: Artificial sequence
<220> FEATURE:
<223> OTHER INFORMATION: Synthesized oligonucleotide

<400> SEQUENCE: 3
aaaccaacgg taagtgaaat g                                                21

<210> SEQ ID NO 4
<211> LENGTH: 18
<212> TYPE: DNA
<213> ORGANISM: Artificial sequence
<220> FEATURE:
<223> OTHER INFORMATION: Synthesized oligonucleotide

<400> SEQUENCE: 4
taacagaacg ggataagt                                                    18

<210> SEQ ID NO 5
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 5
```

-continued

```
ccaagtgggt agatttccaa                                               20

<210> SEQ ID NO 6
<211> LENGTH: 17
<212> TYPE: DNA
<213> ORGANISM: Artificial sequence
<220> FEATURE:
<223> OTHER INFORMATION: Synthesized oligonucleotide

<400> SEQUENCE: 6
caaaagctca cttagtt                                                  17

<210> SEQ ID NO 7
<211> LENGTH: 17
<212> TYPE: DNA
<213> ORGANISM: Artificial sequence
<220> FEATURE:
<223> OTHER INFORMATION: Synthesized oligonucleotide

<400> SEQUENCE: 7
ggcttactcc taatggc                                                  17

<210> SEQ ID NO 8
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 8
cttctcacct tgtggtaaat                                               20

<210> SEQ ID NO 9
<211> LENGTH: 20
<212> TYPE: DNA
<213> ORGANISM: Artificial sequence
<220> FEATURE:
<223> OTHER INFORMATION: Synthesized oligonucleotide

<400> SEQUENCE: 9
catttgggaa acggtaaagt                                               20

<210> SEQ ID NO 10
<211> LENGTH: 18
<212> TYPE: DNA
<213> ORGANISM: Artificial sequence
<220> FEATURE:
<223> OTHER INFORMATION: Synthesized oligonucleotide

<400> SEQUENCE: 10
gtggcgcatg cctgtaat                                                 18

<210> SEQ ID NO 11
<211> LENGTH: 18
<212> TYPE: DNA
<213> ORGANISM: Artificial sequence
<220> FEATURE:
<223> OTHER INFORMATION: Synthesized oligonucleotide

<400> SEQUENCE: 11
gcaaggtcaa cctacatt                                                 18

<210> SEQ ID NO 12
<211> LENGTH: 26
<212> TYPE: DNA
<213> ORGANISM: Artificial sequence
```

-continued

```
<220> FEATURE:
<223> OTHER INFORMATION: Synthesized oligonucleotide

<400> SEQUENCE: 12
tggtatatag gttacatcta ttgata                                    26

<210> SEQ ID NO 13
<211> LENGTH: 17
<212> TYPE: DNA
<213> ORGANISM: Artificial sequence
<220> FEATURE:
<223> OTHER INFORMATION: Synthesized oligonucleotide

<400> SEQUENCE: 13
gctacttgcc atttgac                                              17
```